(12) United States Patent
Kok et al.

(10) Patent No.: US 12,712,068 B2
(45) Date of Patent: Aug. 18, 2026

(54) FEATURE RECOGNITION AND DEPTH GUIDANCE USING INTRAOPERATIVE OCT

(71) Applicant: Leica Instruments (Singapore) Pte. Ltd., Singapore (SG)

(72) Inventors: Alvin Kok, Singapore (SG); John Perng, St. Gallen (CH); Jiarong Wu, Singapore (SG)

(73) Assignee: Leica Instruments (Singapore) Pte Ltd., Singapore (SG)

( * ) Notice: Subject to any disclaimer, the term of this patent is extended or adjusted under 35 U.S.C. 154(b) by 217 days.

(21) Appl. No.: 18/554,818

(22) PCT Filed: Apr. 12, 2022

(86) PCT No.: PCT/EP2022/059804
§ 371 (c)(1),
(2) Date: Oct. 11, 2023

(87) PCT Pub. No.: WO2022/219006
PCT Pub. Date: Oct. 20, 2022

(65) Prior Publication Data

US 2024/0194329 A1 Jun. 13, 2024

(51) Int. Cl.
*G16H 30/40* (2018.01)
*A61B 90/00* (2016.01)
(Continued)

(52) U.S. Cl.
CPC ............. *G16H 30/40* (2018.01); *A61B 90/20* (2016.02); *A61F 9/007* (2013.01); *G06T 7/0014* (2013.01);
(Continued)

(58) Field of Classification Search
None
See application file for complete search history.

(56) References Cited

U.S. PATENT DOCUMENTS

| | | | | |
|---|---|---|---|---|
| 9,910,958 | B2 | 3/2018 | Mielekamp et al. | |
| 2011/0299034 | A1* | 12/2011 | Walsh | A61B 3/132 351/206 |

(Continued)

FOREIGN PATENT DOCUMENTS

| | | |
|---|---|---|
| JP | 2018192287 | 12/2018 |
| WO | 2014175853 A1 | 10/2014 |

(Continued)

OTHER PUBLICATIONS

He et al. (Deep Complementary Joint Model for Complex Scene Registration and Few-shot Segmentation on Medical Images, Computer Vision and Pattern Recognition, 2020) (Year: 2020).*

*Primary Examiner* — Kyle Zhai
(74) *Attorney, Agent, or Firm* — 2SPL Patent Attorneys PartG mbB; Yong Beom Hwang

(57) ABSTRACT

An apparatus for processing image data is disclosed. The apparatus includes one or more processors. The apparatus determines a feature in a cross-sectional image of a live tissue. The apparatus determines a superimposed image by superimposing a reference on the cross-sectional image or a subsequent cross-sectional image of the live tissue. The reference is based on the determined feature. An output interface outputs image data of the superimposed image for display.

14 Claims, 8 Drawing Sheets

(51) Int. Cl.

| | |
|---|---|
| ***A61B 90/20*** | (2016.01) |
| ***A61F 9/007*** | (2006.01) |
| ***G06T 7/00*** | (2017.01) |
| ***G06T 7/55*** | (2017.01) |
| ***G06T 11/00*** | (2026.01) |

(52) U.S. Cl.

CPC ................ *G06T 7/55* (2017.01); *G06T 11/00* (2013.01); *A61B 2090/364* (2016.02); *A61B 2090/3735* (2016.02); *A61B 2090/378* (2016.02); *G06T 2200/24* (2013.01); *G06T 2207/10101* (2013.01); *G06T 2207/10132* (2013.01); *G06T 2207/20092* (2013.01); *G06T 2207/30041* (2013.01); *G06T 2210/41* (2013.01)

(56) References Cited

U.S. PATENT DOCUMENTS

| | | | | |
|---|---|---|---|---|
| 2014/0063447 | A1* | 3/2014 | Piotrowski ............ | A61B 3/102 351/206 |
| 2014/0160264 | A1 | 6/2014 | Taylor et al. | |
| 2016/0042248 | A1 | 2/2016 | Endo et al. | |
| 2016/0089020 | A1 | 3/2016 | Gomi et al. | |
| 2018/0225830 | A1* | 8/2018 | Gopinath .................. | G06T 5/50 |
| 2018/0360655 | A1 | 12/2018 | Berlin | |
| 2019/0274542 | A1* | 9/2019 | Imamura ................ | A61B 3/102 |
| 2019/0388271 | A1* | 12/2019 | Abt .......................... | A61B 3/14 |
| 2021/0038071 | A1* | 2/2021 | Tatara .................. | A61B 3/1225 |

FOREIGN PATENT DOCUMENTS

| | | | |
|---|---|---|---|
| WO | 2014192520 | A1 | 12/2014 |
| WO | 2014203901 | A1 | 12/2014 |

* cited by examiner

FEATURE RECOGNITION AND DEPTH GUIDANCE USING INTRAOPERATIVE OCT

TECHNICAL FIELD

Examples disclosed herein relate to surgical apparatuses such as microscopes and processing of live tissue images.

BACKGROUND

Modern surgical apparatuses may allow users to visualize different anatomical features of varying dimension. It can be challenging to improve user experiences with medical apparatuses, such as surgical microscopes, for example due to the difficulty in intuitively grasping the scale of anatomical features. For example, microscopic features of tissue samples may be difficult to resolve in various imaging methods. The instrumentation intended to treat live tissue, particularly on the microscopic scale, may require delicate and precise control.

SUMMARY

It may be desirable to be able to provide visual cues to aid in the interpretation of images of live tissue. Such visual cues may reduce patient trauma and enable precise treatments of diseased tissue, particularly by providing guidance to a medical practitioner. It is desirable to provide an instrument user such as a medical professional or surgeon with optimally informative image content for analysis or surgical intervention, particularly of live tissue. Precise control of an instrument can be aided by providing visual cues and information that may be difficult to interpret in a raw image. Apparatuses, surgical microscopes, and methods of image guidance are disclosed herein to address such issues.

Herein is disclosed an apparatus for determining image data of tissue as defined in claim 1. Herein is disclosed a non-destructive imaging device as defined in claim 12. Herein is disclosed a surgical microscope as defined in claim 13. Herein is disclosed a method of determining an image as defined in claim 14.

Herein is disclosed an apparatus for processing image data, comprising one or more processors. The apparatus determines a feature in a cross-sectional image of a live tissue; and determines a superimposed image by superimposing a reference on the cross-sectional image or a subsequent cross-sectional image of the live tissue. The reference is based on the determined feature. The apparatus includes an output interface configured to output image data of the superimposed image for displaying the superimposed image. An output interface might be, for example, a display interface for connecting an external monitor. A reference superimposed on a cross-sectional image can aid a medical practitioner in understanding the scale of features in order to reduce the risk of patient trauma.

The apparatus can be configured such that determining the superimposed image includes superimposing a second reference on the cross-sectional image or the subsequent cross-sectional image. The second reference can be determined by a second feature of the cross-sectional image or an offset of the reference. A second reference superimposed on a cross-sectional image can aid a medical practitioner in understanding the scale of features in order to reduce the risk of patient trauma.

The second reference can be offset from the reference by 20-500 μm, for example. Anatomical features in the submillimeter size range can be particularly challenging for a medical practitioner to grasp. References in the size range can greatly aid in guiding treatment procedures to reduce the risk of patient trauma.

The reference can include a plurality of points along a line. A reference in the form of a plurality points along a line can intuitively highlight for a medical practitioner an edge of an anatomical structure in cross-section. Such references aid in guiding treatment procedures to reduce the risk of patient trauma.

The apparatus can receive real time data, and determine the subsequent cross-sectional image based on the real time data. References as described herein, provided in real-time images, can greatly aid in guiding treatment procedures to reduce the risk of patient trauma.

The apparatus can move at least one of the reference or the second reference, based on user input. Allowing adjustment of the reference(s) can allow the practitioner to adapt the reference to better provide highlighted spatial information relevant to the particular procedure. This can aid in guiding treatment procedures to reduce the risk of patient trauma.

The apparatus can accept user input for adjusting at least one of the reference or the second reference, including at least one of: offsetting the plurality of points, offsetting a second plurality of points of the second reference, adjusting a first curvature of the first plurality of points, adjusting a second curvature of the second plurality of points, adjusting a first path of the first plurality of points, or adjusting a second path of the second plurality of points. Allowing adjustment of the reference(s) can allow the practitioner to adapt the reference to better provide highlighted spatial information relevant to the particular procedure. This can aid in guiding treatment procedures to reduce the risk of patient trauma.

The apparatus can determine a stable region of the feature, and update the reference based on the stable region of the feature. Allowing the reference(s) to be updated can reduce errors in identifying features in cross-section. This can aid in reducing the risk of patient trauma.

The apparatus can determine the feature based on at least one of: image recognition, machine learning, threshold determination, or edge detection. References, which are based on features observable in cross-sectional images of live tissue, can aid in guiding treatment procedures to reduce the risk of patient trauma.

The apparatus can receive real time data from at least one of optical coherence or ultrasound, and update at least one of the cross-sectional image or the subsequent cross-sectional image in real time. Allowing the images and/or reference(s) to be updated can reduce errors in identifying features in cross-section. This can aid in reducing the risk of patient trauma.

The apparatus can include a display for displaying the superimposed image. The display can include a user interface. Providing a user interface, e.g. for accepting user input, can provide an easier user experience and reduce operator fatigue, reducing the risk of patient trauma in sensitive procedures.

At least one of the reference and the second reference can include a curved line segment and at least one highlighted point on the curved line segment. The at least one highlighted point can receive user input for adjusting at least one of the respective first and second references. Providing a user interface closely linked to the image and referenced feature, e.g. for accepting user input, can provide an easier user experience and reduce operator fatigue, reducing the risk of patient trauma in sensitive procedures.

Herein is disclosed a non-destructive imaging device, comprising the apparatus as described above. The non-destructive imaging device can determine the cross-sectional image and the subsequent cross-sectional image of the live tissue. References as described herein, provided in images obtained by non-destructive imaging means, can greatly aid in guiding treatment procedures to reduce the risk of patient trauma.

Herein is disclosed a surgical microscope, comprising the non-destructive imaging device. The non-destructive imaging device can include an optical coherence imaging device configured to determine the cross-sectional image of the live tissue. References as described herein, provided in images obtained by OCT, can greatly aid in guiding treatment procedures to reduce the risk of patient trauma.

Herein is disclosed a method of image guidance, comprising determining a feature in a cross-sectional image of a live tissue, determining a superimposed image by superimposing a reference on the cross-sectional image or a subsequent cross-sectional image of the live tissue. The reference can be based on the determined feature. The method also includes outputting image data of the superimposed image for displaying the superimposed image. References as described herein, provided in cross-sectional images of live tissue, can greatly aid in guiding treatment procedures to reduce the risk of patient trauma.

SHORT DESCRIPTION OF THE FIGURES

Some examples of apparatuses and/or methods will be described in the following by way of example, and with reference to the accompanying figures, in which.

DETAILED DESCRIPTION

Various examples will now be described more fully with reference to the accompanying drawings in which some examples are illustrated. In the figures, which are not to be assumed to be to scale, the thicknesses of lines, layers and/or regions may be exaggerated for clarity.

As used herein, the term "and/or" includes any and all combinations of one or more of the associated listed items and may be abbreviated as "/". Herein, a trailing "(s)" indicates one or more; for example processor(s) indicates one or more processors.

Herein, some aspects and/or technical features are described in the context of an apparatus. Technical features described in the context of the apparatus are also understood to describe a corresponding method, for example, in methods of operating the apparatus, operating a surgical microscope, operating a surgical device, image guidance, and/or image processing, for example. Aspects, steps, and/or technical features described in the context of a method also describe a corresponding technical feature of a corresponding apparatus. For example, determinations, as may be described with respect to a method and/or function, may be done by processor(s) of an apparatus, thereby effectively disclosing the apparatus configured to perform the function and/or method. An apparatus described herein as performing a function or step within a method is a disclosure of performing the function and/or method as well.

Figure 1:
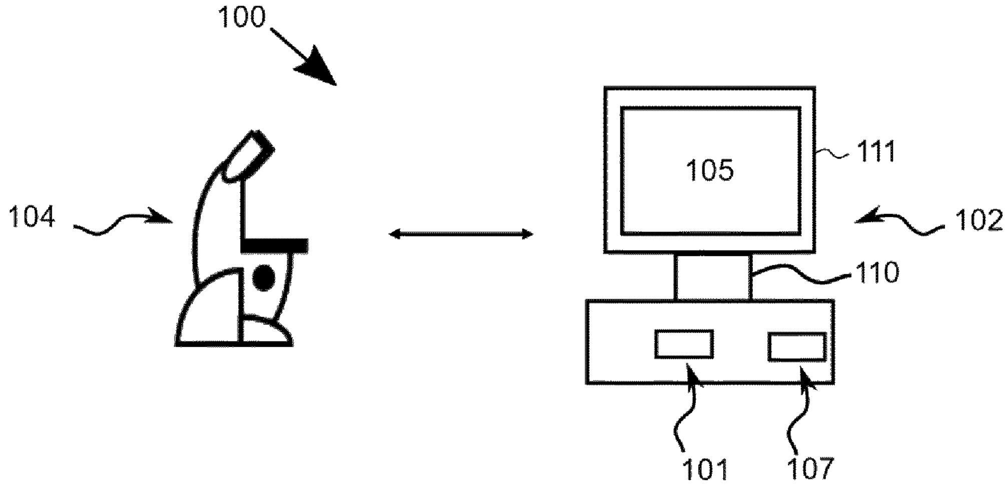
FIG. 1 illustrates a surgical microscope, according to embodiments described herein.

FIG. 1 illustrates an apparatus 102 for processing image data. The apparatus 102 has at least one processor 101. The apparatus 102 may be coupled to an imaging device 104, and/or may be part of a surgical microscope 100. The apparatus 102 can include an output interface 110 which can output image data for display. For example, the image data is transmitted to a display 111. The apparatus 102 and/or surgical microscope 100 may include the display 111 for displaying an image(s) 105, encoded by the image data. The display 111 can be, for example, a 2-D screen, a 3-D screen, or a digital viewer, and may include a touch sensitive screen for user input.

The at least one processor 101 can be programmed for processing image data and/or controlling the display 111. For example, the at least one processor 101 can control a display 111 according to the methods described herein. The processor(s) 101 can process image data, such as to update or change the image data. The display 111 can be configured to receive image data.

The imaging device 104 may be a non-destructive imaging device such as for acquiring optical coherence tomography (OCT) images or ultrasound images. The imaging device 104 may determine cross-sectional images. For example, the imaging device 104 acquires and/or determines cross-sectional images in real time. The cross-sectional images can have a depth component. For example, the imaging device 104 is an OCT microscope, which may be adapted for eye surgery.

Figure 2:
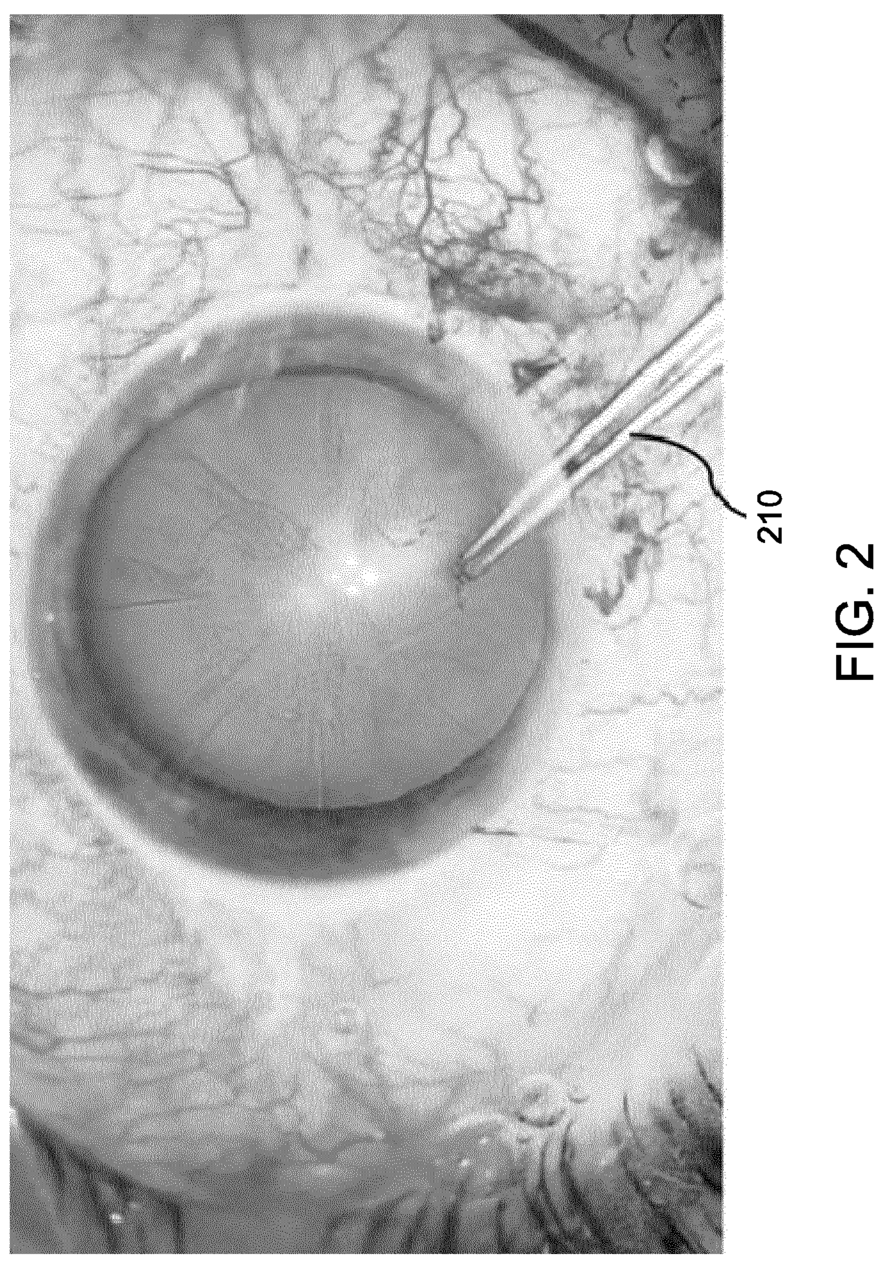
FIG. 2 illustrates an image of an eye, according to embodiments described herein.

FIG. 2 illustrates an image of an eye. FIG. 2 is a visible light reflection image. From FIG. 2, which shows a medical instrument 210, it can be appreciated that it can be challenging to determine depth information from a visible light reflection image. It is desirable to have images which provide intuitive depth information to reduce the risk of patient trauma.

Figure 3:
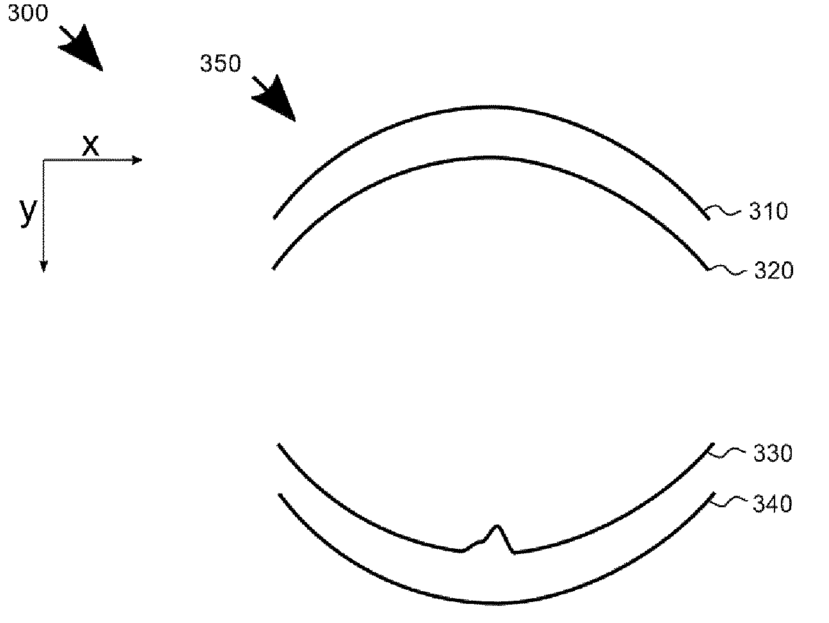
FIG. 3 illustrates an OCT image, according to embodiments described herein.

FIG. 3 is for illustrating some features of OCT images of an eye. The OCT image 300 is representational of a cross-sectional image. The OCT image 300 represented in FIG. 3 has a depth component, y. The depth direction y is shown in FIG. 3, in the vertical direction, and the horizontal direction, x, is also shown. FIG. 3 shows a first feature 310 of an eye 350, in cross-section. Features which are observable in OCT images can be edges and/or interfaces, e.g. between materials of different refractive index. Features observable in ultrasound may also be interfaces and/or edges, e.g. between materials of different acoustic impedance. For example, at the interface of the front surface of the eye and the environment (air), there is an interface and/or edge which appears as a feature 310 in an OCT image. The feature can arise based on the different refractive indices at the interface of the cornea and air. During some procedures, live tissue, such as the cornea may be removed. For example, the feature 310 of FIG. 3 can be the front surface of the cornea. A second feature 320 shown in FIG. 3 can be at the edge or interface of the cornea and the anterior chamber, e.g. at an inner edge of the cornea.

For illustrative purposes, FIG. 3 also shows features at the posterior cavity of the eye. For example, a third feature 330 can be at an edge of the retina or at a retinal layer, e.g. at an inner layer of the retina. A fourth feature 340, for example, can be at the interface or edge of the retina and the choroid, e.g. an edge at an outer layer of the retina. The retina may have multiple layers or edges, between the outermost and innermost layers or edges of the retina, which may also determinable from cross-sectional imaging techniques, e.g. of live tissue. Features determinable and/or observable in the image may be layers, e.g. layers and/or edges associated with anatomical layers of the eye, particularly when the images are cross-sectional images.

The apparatus 102 may be configured to determine a feature in a cross-sectional image of live tissue. For example, the apparatus 102 may be configured to display a cross-sectional image in real-time and to display the feature. The apparatus 102 may acquire images in real-time and/or repeatedly, e.g. so that after an initial cross-sectional image is acquired/determined, a subsequent cross-sectional image of the live tissue is acquired/determined.

It is to be appreciated that FIG. 3 is an illustration in which the features 310, 320, 330, 340 may be easily recognized, e.g. as layers of the cornea 310, 320 or retina 330, 340. It is also to be appreciated that in actual images acquired by various imaging techniques such as nondestructive techniques like OCT and ultrasound, there can be noise, spurious signals, artifacts, multiple reflections, interferences and the like which may make image interpretation difficult.

FIG. 3 is for illustrative purposes and shows simultaneously features of the anterior of the eye such as an edge 310 of the corona, and posterior features such as an edge 330 of the retina. Imaging techniques such as OCT and/or ultrasound may provide high resolution images of parts of the eye. Imaging techniques may provide, for example, high resolution cross-sectional images of an anatomical structure, such as an eye, possibly in real time.

Figure 4:
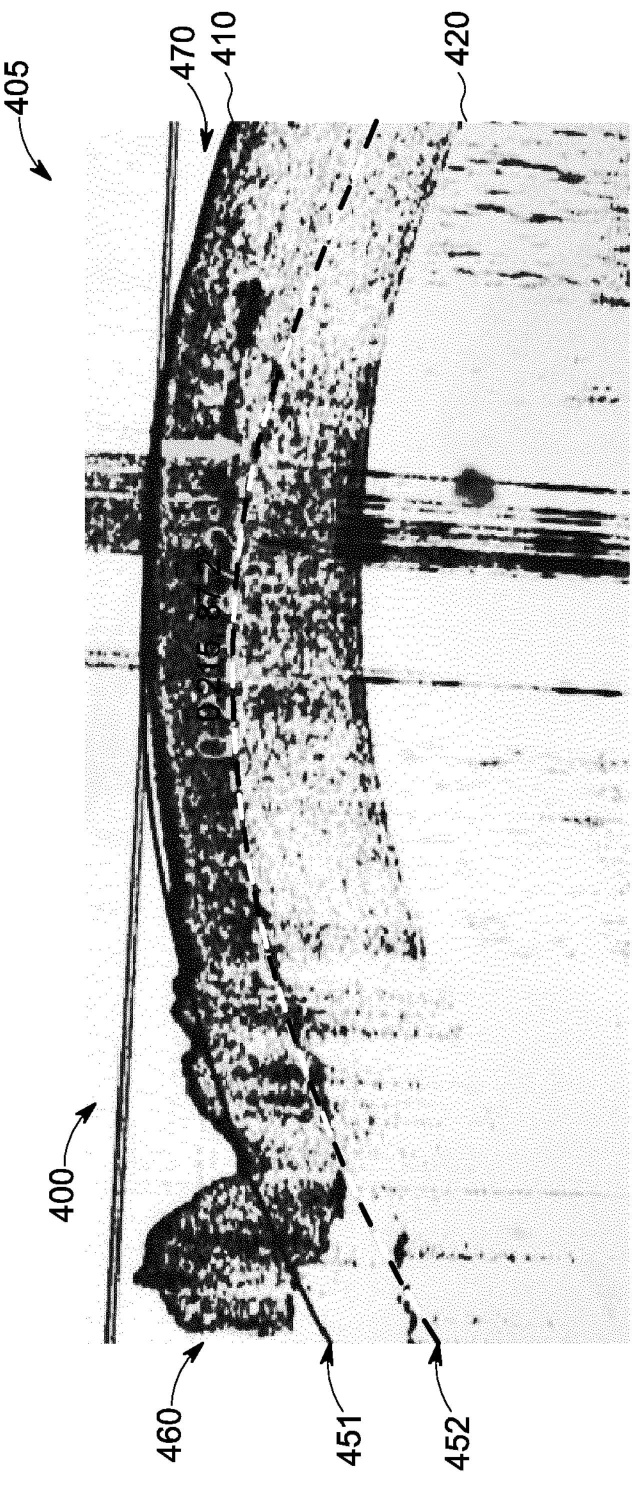
FIG. 4 illustrates a superimposed image, according to embodiments described herein.

FIG. 4 illustrates a superimposed image, according to embodiments described herein. FIG. 4 illustrates an intraoperative image of living tissue. FIG. 4 can be an OCT image of an eye during a surgical procedure. FIG. 4 is a cross-sectional image. Features which can be seen in FIG. 4 can be an outer edge 410 of the eye and an inner edge 420, such as outer and inner edges of the cornea. The cornea may have multiple layer which may appear as features in an OCT image.

A superimposed image 400 is determined by superimposing references 451, 452, in this case, two curves, on the cross-sectional image, 405, at the edge 410, and at an offset of the edge 410. The first reference 451, in this case, is a solid line. The second reference 452, in this example, is a dashed line.

The cross-sectional image 405 may include features, such as layers and/or edges 410, 420. The apparatus 102 may be configured and/or programmed to determine features of cross-sectional images of live tissue. The superimposed image 400 can be determined by superimposing a reference, e.g. the first reference 451, on the cross-sectional image 405. Alternatively/additionally, superimposed image 400 can be determined by superimposing a reference, e.g. the first reference 451, on a subsequent cross-sectional image. The reference, e.g. the first reference 451 in this example, can be based on the edge 410 of the feature as determined in the cross-sectional image 405.

The apparatus 102 may determine a superimposed image 400 by superimposing a reference on a cross-sectional image of the live tissue. The reference 451 may be based on the determined feature or edge of a cross-sectional image, and may be superimposed on the cross-sectional image or a subsequent cross-sectional image. The reference 451 can be for indicating a feature, or a previous feature which may be subsequently absent. The reference 451 can be a line that traces a feature as determined by the apparatus. The reference 451 can be a plurality of points along a line, for example. The reference 451 can trace an edge or layer of the eye which is observable in the image. The reference 451 can provide greater contrast than what is present in the cross-sectional image. For example, some of the features observable with imaging techniques may be faint and/or noisy, such as the various layers of the eye. Providing a reference 451 can highlight a feature (e.g. a layer) of a cross-sectional image to reduce the risk of a medical practitioner misinterpreting an image, or overlooking important features within the image.

A second reference can be superimposed on the cross-sectional image 405 or a subsequent cross-sectional image, e.g to determine the superimposed image 400. In the example of FIG. 4, the second reference 452 is a dashed line. A second reference 452 can be determined by a second feature such as an edge of the cross-sectional image 405. Alternatively/additionally, the second reference 452 can be determined by an offset applied to the first reference and/or a first edge 410. One or more references 451, 452 are contemplated.

A reference, such as each of the first and second references 451, 452 can include a plurality of points along a line. A reference can include points that form a line. For example, the first reference 451 is a plurality of points forming a line, and the second reference 452, which is a dashed line, includes a plurality of points along a line. When the reference is used to highlight an edge or layer which is observable in a cross-sectional image, or an offset therefrom, a medical professional can be aided by references which have a similar form or shape of the features as they are determined to appear in the cross-sectional images.

The apparatus 102 can receive real-time data and determine a subsequent cross-sectional image based on the real-time data. The reference(s) can be superimposed on the subsequent cross-sectional image(s). It is also possible that the reference(s) is updated based on user input and/or received/acquired data, such as real-time data (e.g. from OCT, ultrasound, or other imaging techniques, particularly nondestructive imaging techniques). Nondestructive imaging techniques reduce patient trauma. OCT and ultrasound are effective at providing cross-sectional images that have a depth component. Real-time data is helpful in providing up-to-the-second (plus or minus) accurate spatial information to a medical practitioner to aid in precise surgical interventions.

Each reference can be superimposed on the image(s). For example, at least one additional reference can be superimposed on the image at an offset of from approximately 10-500 μm, or from 10-300 μm, from a first reference 451 and/or a first determined edge 410. Enabling the display of references at offsets can aid a medical practitioner in performing sensitive and precise surgical procedures. Particularly, when the offsets are in the depth direction, y, references 451, 452 can provide a medical practitioner with a better idea of the dimensions of the features involved, e.g. and may reduce the risk of patient trauma during sensitive procedures.

FIG. 4 illustrates also an unsmooth region 460 of the OCT image which has been subjected to a surgical treatment. At the opposite side of the OCT image, the edge, near stable region 470, of the feature is smooth. The apparatus 102 may determine and/or recognize a stable region 470 of the feature, e.g. at a part of the edge that is not directly subjected to surgical treatment. Alternatively/additionally, the apparatus 102 may determine and/or recognize an unstable region (e.g. the unsmooth region 460) of the feature. By determining a stable region 470 or a treated (or "unstable" region, e.g. a region undergoing changes), the apparatus 102 can improve the stability of the reference 451 for the user. This may allow a medical practitioner to easily recognize the effects of the treatment on the tissue, e.g. by having confidence that the reference 451 is stable.

For example, the apparatus 102 can update the reference 451 in a subsequent image based on the stable region 470, e.g. based on recognition of the stable region 470 of the edge 410. Alternatively/additionally, the apparatus may update the superimposed image while maintaining the reference 451, e.g. by processing imaging data, possibly in real-time.

A user may input a desired region (e.g. the stable region 470) in order to allow the apparatus to continue to update the position of the reference 451, e.g. in a subsequent image such as in real-time. While procedures are being carried out, some regions (e.g. the unsmooth region 460) of the tissue may undergo structural changes such that some features along the edge 410 deviate from the path of the original reference 451. It can be useful for a practitioner to be able to select regions of the image or reference which can anchor subsequent placement of the reference(s).

FIGS. 5A-5E illustrate anatomical structures of the eye. FIGS. 5A-5E illustrate different layers and/or regions of the eye 500 which may be subjected to surgical procedures. For example, in cornea transplants, it may be desirable to remove a precise thickness of a patient's tissue. The thicknesses of the corneal layers which may require treatment including possible removal and/or replacement can be on the scale of micrometers. There is a desire to reduce the risk of patient trauma and surgical and post-surgical complications, in sensitive eye surgeries in particular. The use of references as described herein may contribute to reducing the risk of patient trauma. In surgery, particularly cornea surgery, it can be challenging to correctly estimate the depth of insertion of an instrument.

Figures 5A, 5B, 5C, 5D, 5E:
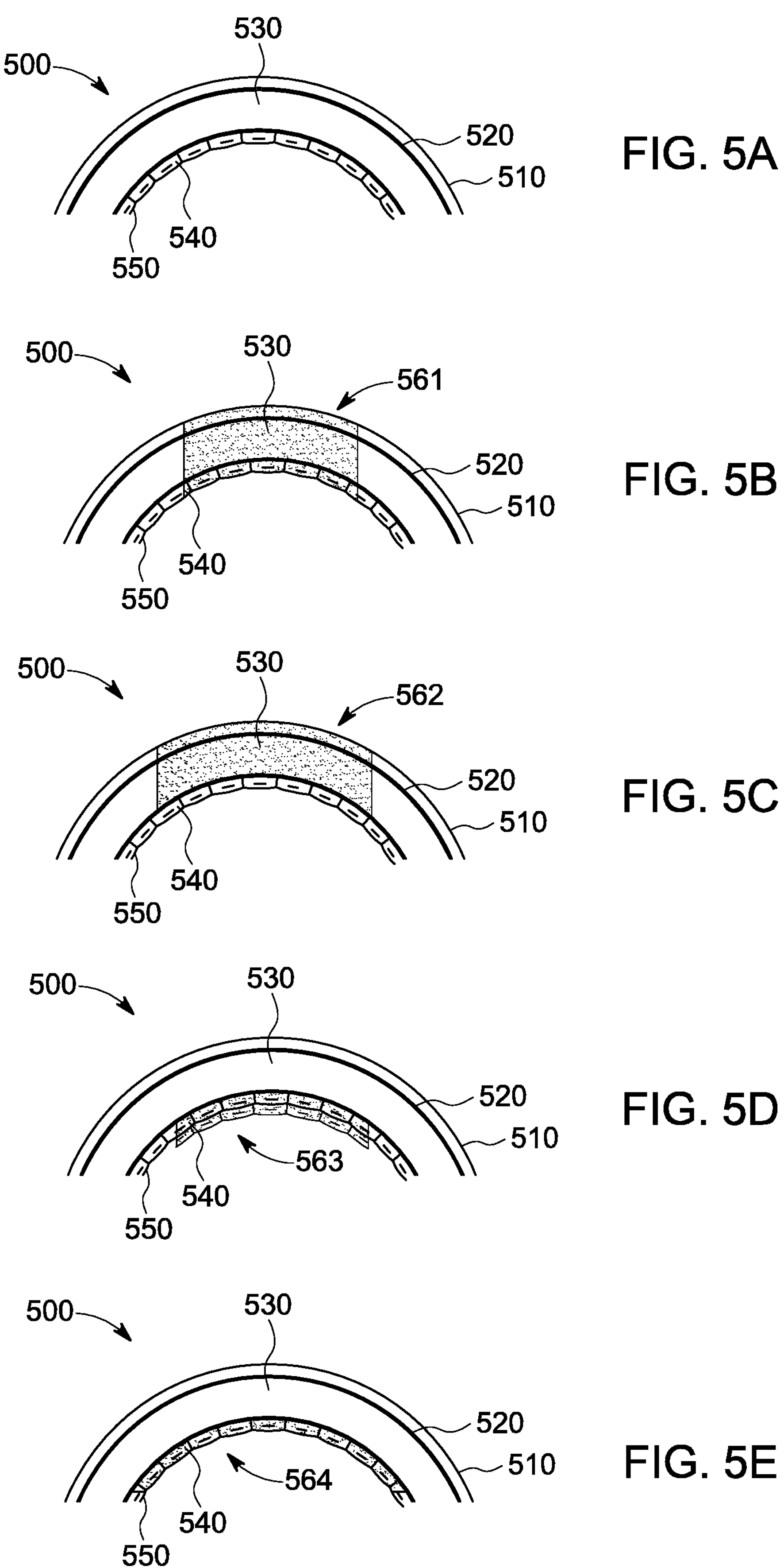
FIGS. 5A-5E illustrates anatomical structures of the eye, according to embodiments described herein.

FIG. 5A shows the epithelium 510, the Bowman layer 520, the stroma 530, the Descemet membrane 540, and the endothelium 550.

FIG. 5B shows some anatomical structures of the eye. In FIG. 5B, a first region 561 is highlighted, relevant to a penetrating keratoplasty procedure. For example, the first region 561 may be removed and replaced in a penetrating keratoplasty procedure.

FIG. 5C shows anatomical structures of the eye, and highlights a second region 562, relevant to a deep anterior lamellar keratoplasty (DALK) procedure. It may be desirable in some procedures, such as a DALK graft procedure, to remove and/or replace tissue while leaving the Descemet membrane 540 intact.

FIG. 5D shows anatomical structures of the eye, and highlights a third region 563, relevant to a Descemet's stripping endothelial keratoplasty (DSAEK) procedure. It may be desirable in some procedures, such as a DSAEK graft procedure, to selectively remove the Descemet membrane 540 and endothelium 550. Donor corneal endothelium and/or donor corneal stroma can be subsequently transplanted. The procedure can involve transplantation of tissue that is approximately 100-200 microns thick.

FIG. 5E shows anatomical structures of the eye, and highlights a fourth region 564 relevant to a Descemet's membrane endothelial keratoplasty (DMEK) procedure. The grafted tissue of a DMEK procedure may be approximately 10-15 μm thick.

The examples shown in FIGS. 5B-5E illustrate the microscopic precision with which medical practitioners may treat tissue, particularly living tissue. During eye surgery, various structures such as layers of the eye may be treated, such as removed and/or replaced. Anatomical structures of the eye may be microscopically thin and fragile. The superimposed images and references described herein may aid medical practitioners and reduce the risk of patient trauma.

Figure 6:
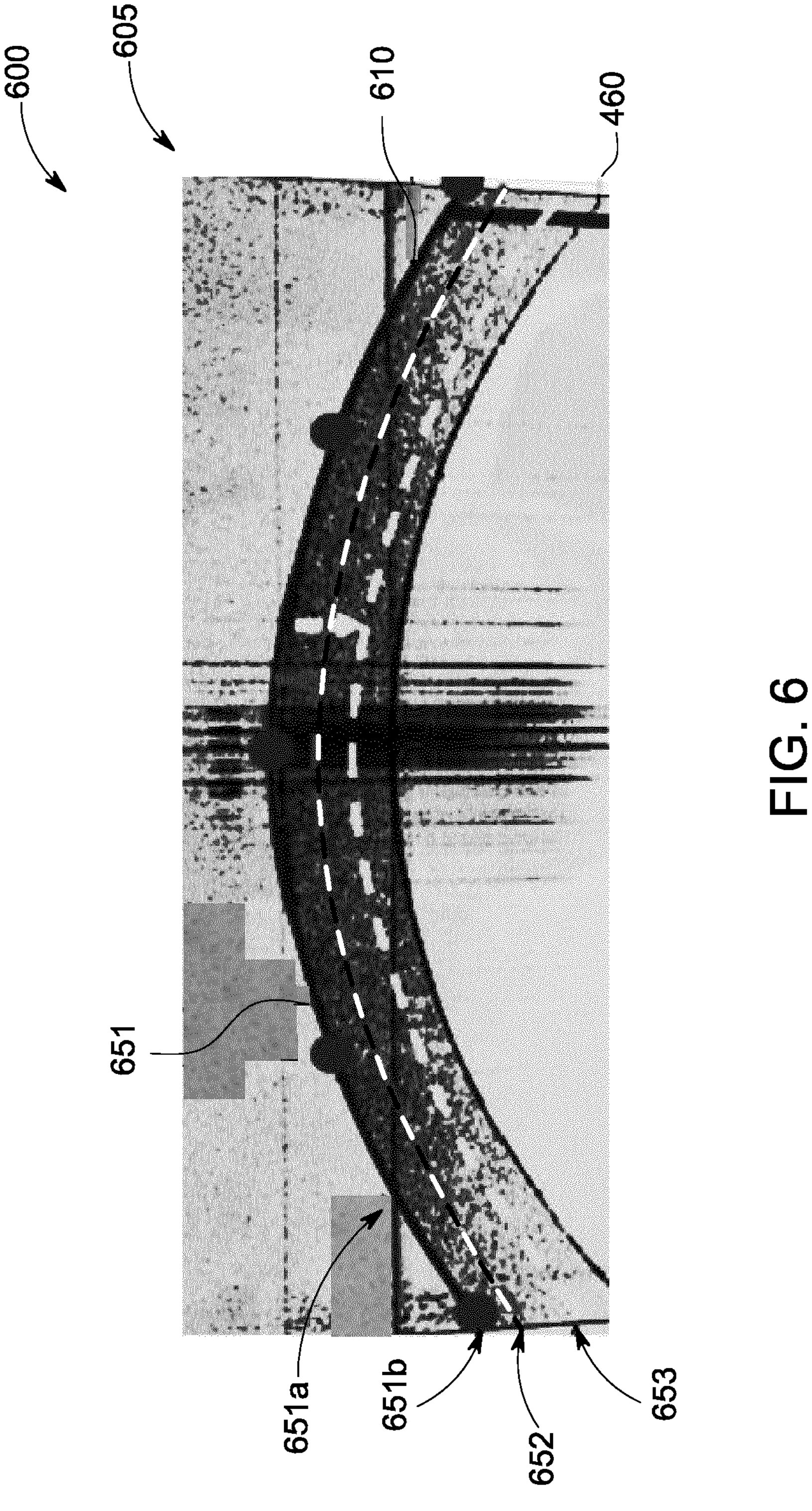
FIG. 6 illustrates a superimposed image, according to embodiments described herein.

FIG. 6 illustrates a superimposed image, according to embodiments described herein. FIG. 6 illustrates an intraoperative image of living tissue. FIG. 6 can be an OCT image of an eye during a surgical procedure. FIG. 6 is a cross-sectional image. FIG. 6 shows an outer edge 610 of an eye and an inner edge 620 of an eye. For example, FIG. 6 can be illustrative of references being used to highlight layers of the cornea.

The cross-sectional image 605 may include various features such as edges 610, 620. The apparatus 102 may be configured and/or programmed to determine edges of cross-sectional images of live tissue. The superimposed image 600 can be determined by superimposing a reference, e.g. the first reference 651, on the cross-sectional image 605. Alternatively/additionally, superimposed image 600 can be determined by superimposing a reference, e.g. the first reference 651, on a subsequent cross-sectional image. The reference, e.g. the first reference 651 in this example, can be based on the edge 610 as determined in the cross-sectional image 605.

A superimposed image 600 can be determined by superimposing references 651, 652, 653, on the cross-sectional image, 605. For example, the first reference 651 can be at the outer edge 410, and/or at an outer layer. The second and third references 652, 653 can be at offsets therefrom, such as at 50 μm and 100 μm, respectively. The first reference 451, for example, includes a plurality of points along a line. The second and third references 652, 653 are in this case dashed lines. Any of the references 651, 652, 653 can be stored in memory, recalled from memory, held constant, or adjusted. References can be updated based on real-time data, for example. Alternatively/additionally, any reference 651, 652, 653 can be updated and/or moved based on user input. It is possible that the reference(s) can be moved, such as in order to adjust the path, tortuousness, tortuosity, and/or curvature of the reference. The ability to make such adjustments may allow a medical practitioner to modify references to better highlight sensitive aspects of the anatomy that may require intervention, or may be desirably avoided. The possibility for a user to modify the references can make up for shortcomings such as noise or artefacts from the imaging technique. Alternatively/additionally, a reference can be updated based on real-time data.

The apparatus 102 can accept user input for adjusting at least one of the references 651, 652, 653 (or the only reference in the case there is only one reference). For example, adjusting at least one reference 651, 652, 653 can include at least one of: offsetting the plurality of points (particularly in the depth direction) of the first reference 651, offsetting a second plurality of points of the second reference (particularly in the depth direction), adjusting a first curvature of the first plurality of points, adjusting a second curvature of the second plurality of points of the second reference, adjusting a first path of the first plurality of points, or adjusting a second path of the second plurality of points.

In FIG. 6, the first reference 651 includes a continuous line 651*a* and some dots 651*b* thereon. The display 111 of the apparatus may accept user input, such as by having a touch sensitive interface at the display 111. The dots 651*b* can provide visual indications for a user for accepting touch input. For example, a user can drag a dot 651*b* (e.g. touch and drag) to adjust the reference 651. The reference 651 can be adjusted by an offset, a change of curvature, and/or a change of the path along which the reference 651 extends.

The reference(s) 651, 652, 653 can include a curved line segment (e.g. the dashed lines of the second and third references 652, 653 of FIG. 6). Alternatively/additionally, the reference(s) 651, 652, 653 can include at least one highlighted point on the curved line segment, e.g. the dots 651*b* of FIG. 6. The at least one highlighted point can possibly receive user input, e.g. touch, for adjusting at least one of the references (e.g. the first reference 651 of FIG. 6), particularly when the apparatus 102 includes a display 111 with touch input capability.

Figure 7:
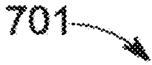
FIG. 7 illustrates images of live tissue, according to embodiments described herein.
Figure 7:
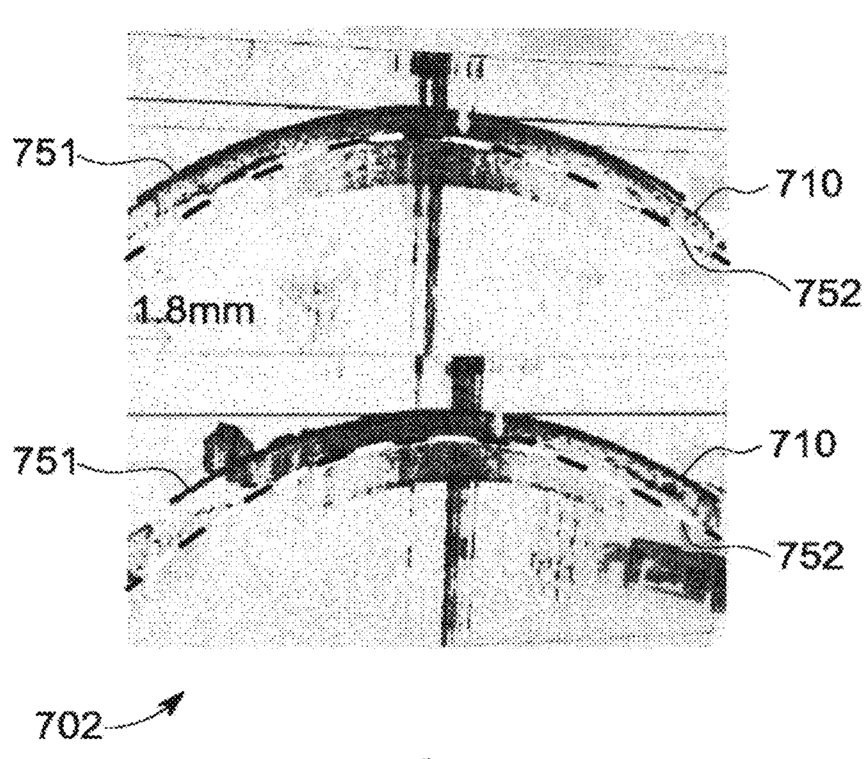

FIG. 7 illustrates images of live tissue, according to embodiments described herein. FIG. 7 illustrates two images, a first image 701 and a subsequent image 702. Each of the images are determined by superimposing at least one reference 751, 752 on cross-sectional images of live tissue taken sequentially. The first image 701 shows an edge 710 which is determined by the apparatus 102. The first reference 751 is based on the determined edge 710. The first reference 751 can be superimposed on the first image 701 and the subsequent image 702. The second reference 752 can be superimposed on the first image 701 and the subsequent image 702. The second reference 752 can be determined from an offset of the determined edge 710 and/or the first reference 751.

The second image 702, or any subsequent image, can be determined by superimposing the first and second references 751, 752 on a cross-sectional image of the live tissue which is acquired subsequent to the first 701.

The references 751, 752 can be held constant, recalled from memory, and/or adjusted, as described herein. References 751, 752 can be updated, such as shifted in position, based on real-time data, for example. The position of references 751, 752 can be adjusted to align with features, such as the edge 710 (and/or with a portion of the edge 710) as determined in subsequent images.

The apparatus 102 can determine the features, such as the edge 710, based on at least one of: image recognition, machine learning, threshold determination, or edge detection. Image recognition can include recognizing a feature of an eye such as a retinal interface and/or a corneal interface.

Figure 8:
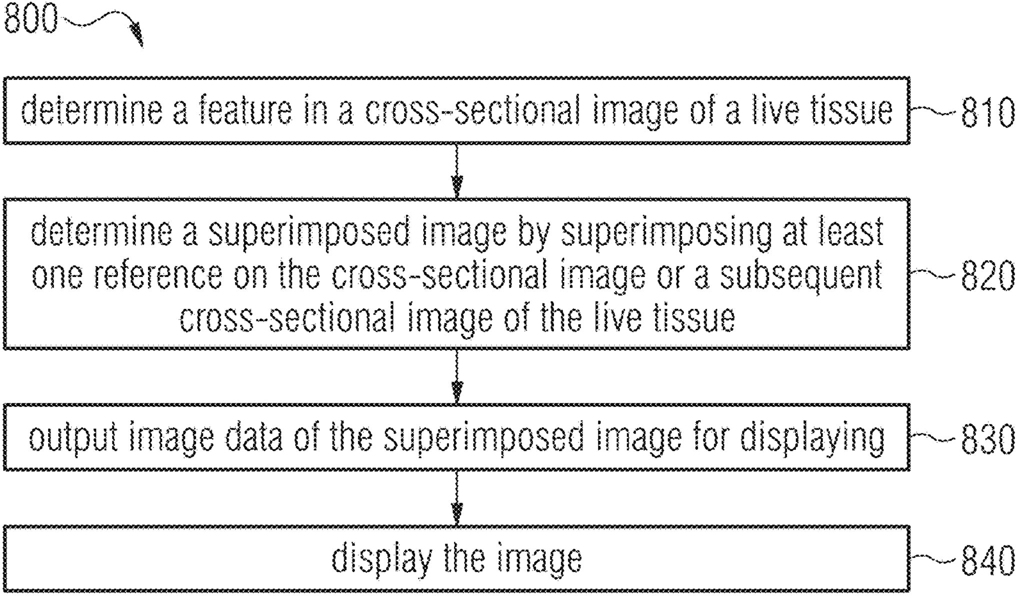
FIG. 8 illustrates a method of image guidance, according to embodiments described herein.

FIG. 8 illustrates a method of image guidance. The method 800 can include determining 810 a feature in a cross-sectional image of a live tissue, and determining 820 a superimposed image by superimposing at least one reference on the cross-sectional image or a subsequent cross-sectional image of the live tissue. The reference(s) can be based on a determined edge and/or layer of tissue. The reference(s) can be along the determined edge.

Alternatively/additionally, a reference can be at an offset from a feature, such as a determined edge and/or other reference. The method can also include outputting 830 image data of the superimposed image for displaying. The image can be displayed 840 on a touch-screen device that allows for direct user input at the display, e.g. for adjusting the reference(s).

Figure 9A:
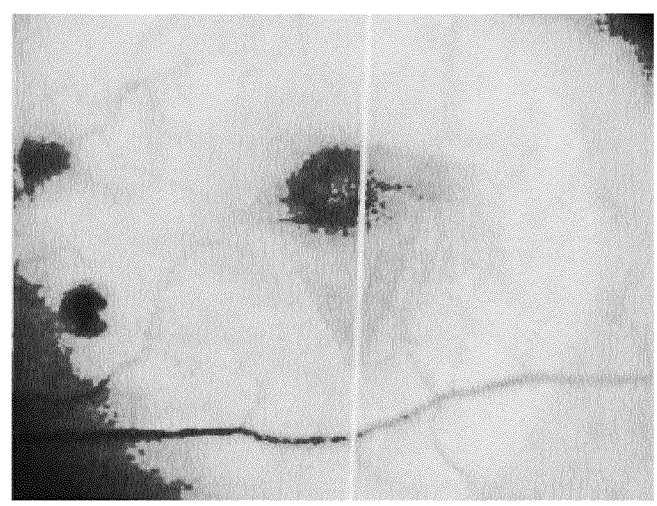
FIGS. 9A and 9B illustrate images of live tissue, according to embodiments described herein.
Figure 9B:
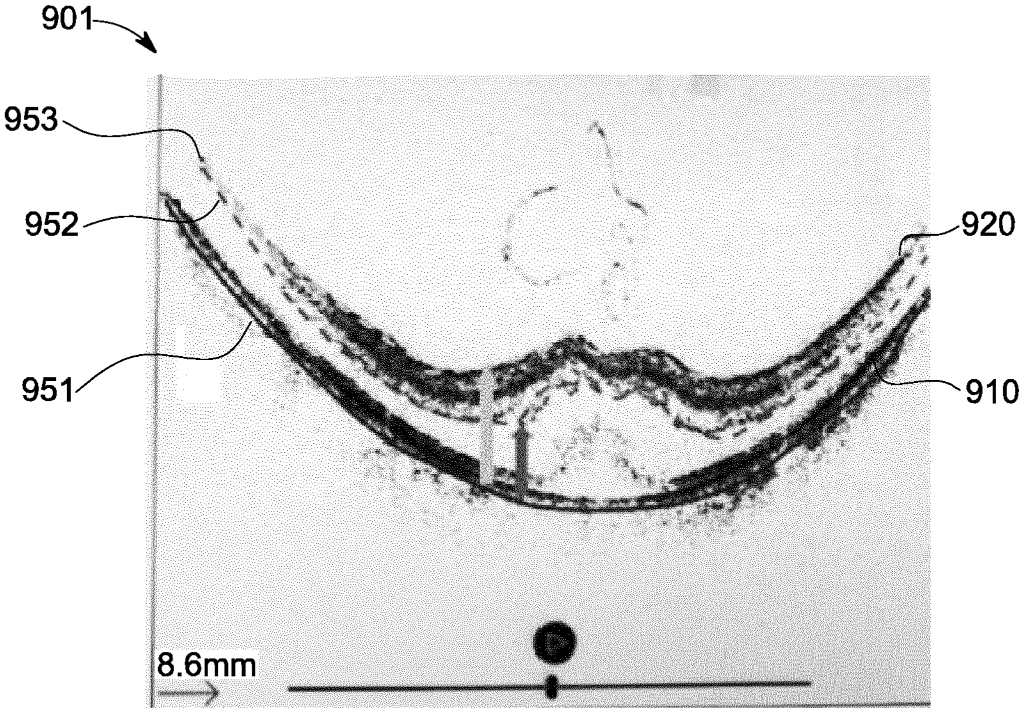

FIGS. 9A and 9B illustrate images of live tissue, according to embodiments described herein. FIG. 9A is a visible light image. FIG. 9B is an OCT image. The OCT image of FIG. 9B is a cross-sectional image 901 which is determined by superimposing at least one reference 951, 952, 953 on a cross-sectional image of live tissue. The first reference 951 can be based on a determined edge 910 or layer of the cross-sectional image. The cross-sectional image may show more than one edge 910, 920 (e.g. of feature(s), e.g. as determined by the apparatus 102 and/or imaging technique). The references 951, 952, 953 can be superimposed on the image 901 and any subsequent image. The second and third references 952, 953 can each be determined by a second or greater number of feature(s) of the cross-sectional image. Alternatively/additionally, reference(s) can be determined by offsetting features, edge, and/or other references.

FIGS. 9A and 9B show cross-sectional images of the posterior eye, including retinal layers. The apparatus 102 and methods described herein may be used to reduce risk of patient trauma in retinal procedures. For example, references may be offset to provide visual cues as to the depth of cross-sectional images, to aid medical practitioners in performing sensitive procedures, such as peeling and/or cutting layers of tissue.

Figure 10:
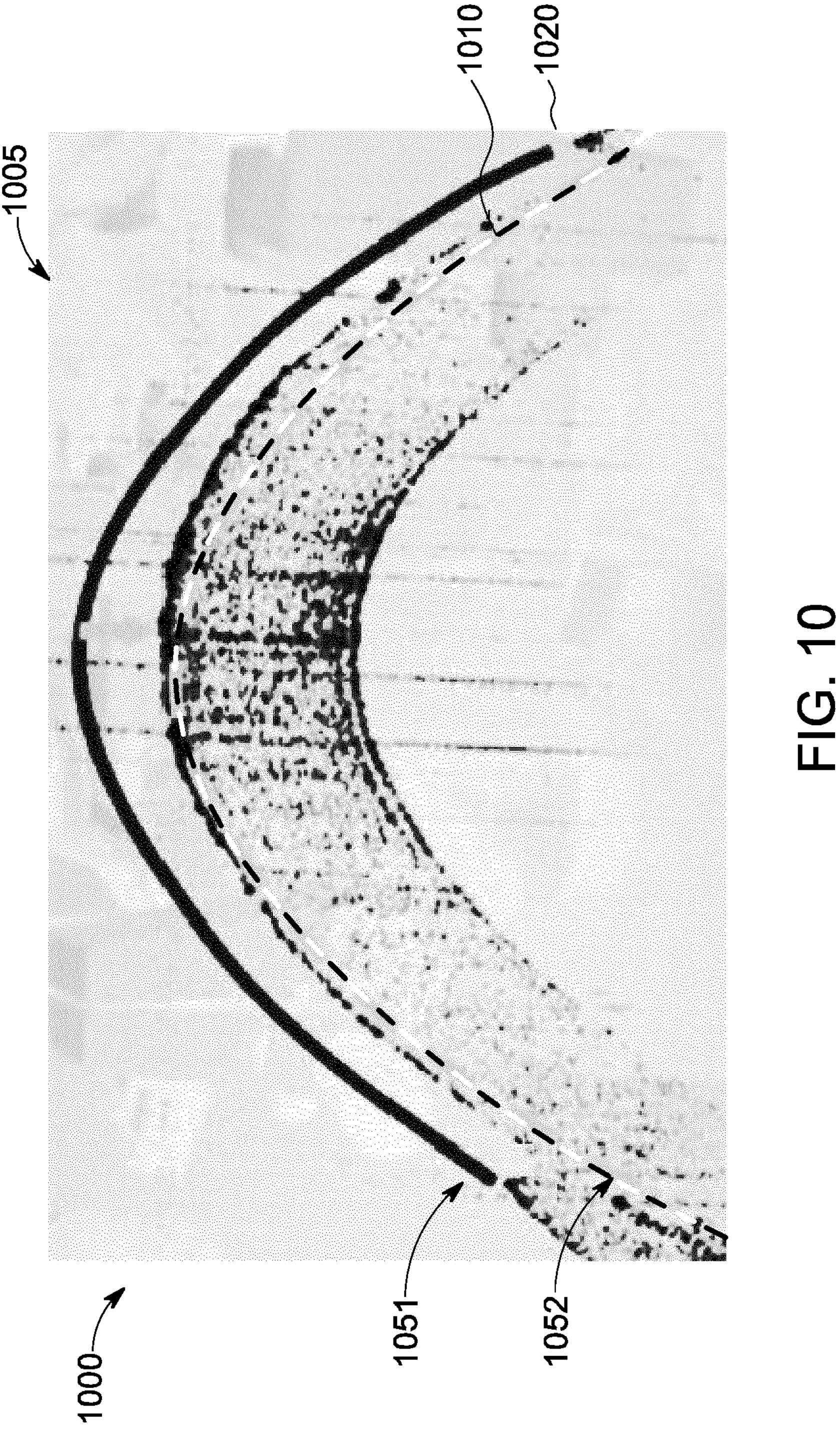
FIG. 10 illustrates a superimposed image, according to embodiments described herein.

FIG. 10 illustrates a superimposed image, according to embodiments described herein. FIG. 10 illustrates an intraoperative image of living tissue. FIG. 1 can be an OCT image of an eye during a surgical procedure. FIG. 10 is a cross-sectional image. FIG. 10 shows at least one edge 1010 or layer of an eye, which is determined by the apparatus 102 (e.g. by a processor thereof).

The superimposed image 1000 can be determined by superimposing reference(s), e.g. first and second references 1051, 1052 on the cross-sectional image 1005.

Alternatively/additionally, superimposed image 1000 can be determined by superimposing a reference, e.g. the first reference 1051, on a subsequent cross-sectional image, which may be determined/acquired in real-time.

A reference, such as the reference 1051 may be based on the edge 1010. A reference, such as reference 1051, may be adjustable, e.g. to have an adjustable curvature. A medical practitioner may change the curvature of a reference in order to provide a visual guide as to a desired curvature outcome at the end of the procedure, for example. Such references, serving for example as visual guides, can be helpful in determining how much tissue to remove and/or transplant. Similarly, references, such as second reference 1052, may be offsets from other references.

References 1051, 1052 may be stored in memory, removed from the display, and later redisplayed.

Herein a reference can be an indicator, e.g. for highlighting a feature of an image. For example, a reference can be a visual marker. For example, a reference can include a continuous line, a dotted line, a dashed line, and the like. A reference may trace a feature, such as an edge or layer of tissue, which is determinable/observable in an image. Alternatively/additionally, a reference can include an arrow. A reference can be used as a visual cue to draw attention, e.g. to a feature of an acquired image.

Herein, a feature can be a layer of tissue, e.g. a layer of tissue shown in cross-section. Alternatively/additionally, a feature can be an edge of a layer of tissue, such as an edge, e.g. an outer edge or inner edge.

The superimposed images described herein may be determinable by the apparatuses as described herein such as with regard to that shown in FIG. 1. The apparatuses described herein are understood to be configured to enable the features and functions related to the superimposed images as described herein, such as the determination of features, layers, and/or edges and modification of references. For example, the apparatus may include a processor(s) configured to determine the superimposed image(s), reference(s), receive real-time data, modify such as move the reference(s), process user input, and generate image data for display, for example.

Herein is disclosed the use of machine learning such as to determine a feature such as an edge or layer of tissue. Machine learning can refer to algorithms and/or statistical models that computer systems may use to perform task(s) possibly without using particularized explicit instructions, instead relying on models and inference. For example, in machine-learning, instead of a rule-based transformation of data, a transformation of data may be used, that is inferred from an analysis of historical and/or training data. For example, the content of images may be analyzed using a machine-learning model or using a machine-learning algorithm.

In order for the machine-learning model to analyze the content of an image, the machine-learning model may be trained using training images as input and training content information as output. By training the machine-learning model with a large number of training images and associated training content information, the machine-learning model learns to recognize the content of the images, so the content of images that are not included of the training images can be recognized using the machine-learning model. The same principle may be used for other kinds of sensor data as well, e.g. OCT data and/or ultrasound data: by training a machine-learning model using training sensor data and a desired output, the machine-learning model learns a transformation between the sensor data and the output, which can be used to provide an output based on non-training sensor data provided to the machine-learning model. Machine-learning models can be trained using training input data. The examples specified above may use supervised learning. In supervised learning, the machine-learning model can be trained using a plurality of training samples. Each training sample may comprise a plurality of input data values, and a plurality of desired output values, i.e. each training sample is associated with a desired output value. By specifying both training samples and desired output values, the machine-learning model learns which output value to provide based on an input sample that is similar to the samples provided during the training.

Alternatively/additionally, semi-supervised learning may be used. In semi-supervised learning, some of the training samples lack a corresponding desired output value. Supervised learning may be based on a supervised learning algorithm, e.g. a classification algorithm, a regression algorithm or a similarity learning algorithm. Classification algorithms may be used when the outputs are restricted to a limited set of values, i.e. the input is classified to one of the limited set of values. Regression algorithms may be used when the outputs may have any numerical value (within a range). Similarity learning algorithms are similar to both classification and regression algorithms, but are based on learning from examples using a similarity function that measures how similar or related two objects are.

Unsupervised learning may be used to train the machine-learning model. In unsupervised learning, (only) input data might be supplied, and an unsupervised learning algorithm may be used to find structure in the input data, e.g. by grouping or clustering the input data, finding commonalities in the data. Clustering is the assignment of input data comprising a plurality of input values into subsets (clusters) so that input values within the same cluster are similar according to one or more (pre-defined) similarity criteria, while being dissimilar to input values that are included in other clusters.

Alternatively/additionally, reinforcement learning may be used to train the machine-learning model. In reinforcement learning, one or more software actors (called "software agents") can be trained to take actions in an environment. Based on the taken actions, a reward is calculated. Reinforcement learning is based on training the one or more software agents to choose the actions such, that the cumulative reward is increased, leading to software agents that become better at the task they are given (as evidenced by increasing rewards).

Furthermore, some techniques may be applied to some of the machine-learning algorithms. For example, representation learning may be used. In other words, the machine-learning model may at least partially be trained using representation learning, and/or the machine-learning algorithm may comprise a feature learning component. Representation learning algorithms, which may be called feature learning algorithms, may preserve the information in their input, but also transform it in a way that makes it useful, often as a pre-processing step before performing classification or predictions. Representation learning may be based on principal components analysis or cluster analysis, for example.

In some examples, anomaly detection (i.e. outlier detection) may be used, which may be aimed at providing an identification of input values that raise suspicions by differing significantly from the majority of input or training data. In other words, the machine-learning model may at least partially be trained using anomaly detection, and/or the machine-learning algorithm may comprise an anomaly detection component.

In some examples, the machine-learning algorithm may use a decision tree as a predictive model. In other words, the machine-learning model may be based on a decision tree. In a decision tree, observations about an item (e.g. a set of input values) may be represented by the branches of the decision tree, and an output value corresponding to the item may be represented by the leaves of the decision tree. Decision trees may support both discrete values and continuous values as output values. If discrete values are used, the decision tree may be denoted a classification tree, if continuous values are used, the decision tree may be denoted a regression tree.

Association rules are a further technique that may be used in machine-learning algorithms. In other words, the machine-learning model may be based on one or more association rules. Association rules are created by identifying relationships between variables in large amounts of data. The machine-learning algorithm may identify and/or utilize one or more relational rules that represent the knowledge that is derived from the data. The rules may e.g. be used to store, manipulate or apply the knowledge.

Machine-learning algorithms are usually based on a machine-learning model. In other words, the term "machine-learning algorithm" may denote a set of instructions that may be used to create, train or use a machine-learning model. The term "machine-learning model" may denote a data structure and/or set of rules that represents the learned knowledge, e.g. based on the training performed by the machine-learning algorithm. In embodiments, the usage of a machine-learning algorithm may imply the usage of an underlying machine-learning model (or of a plurality of underlying machine-learning models). The usage of a machine-learning model may imply that the machine-learning model and/or the data structure/set of rules that is the machine-learning model is trained by a machine-learning algorithm.

For example, the machine-learning model may be an artificial neural network (ANN). ANNS can be systems that are inspired by biological neural networks, such as can be found in a brain. ANNs comprise a plurality of interconnected nodes and a plurality of connections, so-called edges, between the nodes. There are usually three types of nodes, input nodes that receiving input values, hidden nodes that are (only) connected to other nodes, and output nodes that provide output values. Each node may represent an artificial neuron. Each edge may transmit information, from one node to another. The output of a node may be defined as a (non-linear) function of the sum of its inputs. The inputs of a node may be used in the function based on a "weight" of the edge or of the node that provides the input. The weight of nodes and/or of edges may be adjusted in the learning process. In other words, the training of an artificial neural network may comprise adjusting the weights of the nodes and/or edges of the artificial neural network, i.e. to achieve a desired output for a given input. In at least some embodiments, the machine-learning model may be deep neural network, e.g. a neural network comprising one or more layers of hidden nodes (i.e. hidden layers), preferably a plurality of layers of hidden nodes.

Alternatively, the machine-learning model may be a support vector machine. Support vector machines (i.e. support vector networks) are supervised learning models with associated learning algorithms that may be used to analyze data, e.g. in classification or regression analysis. Support vector machines may be trained by providing an input with a plurality of training input values that belong to one of two categories. The support vector machine may be trained to assign a new input value to one of the two categories. Alternatively, the machine-learning model may be a Bayesian network, which is a probabilistic directed acyclic graphical model. A Bayesian network may represent a set of random variables and their conditional dependencies using a directed acyclic graph. Alternatively, the machine-learning model may be based on a genetic algorithm, which is a search algorithm and heuristic technique that mimics the process of natural selection.

Some embodiments relate to a microscope comprising a system as described in connection with one or more of the figures. Alternatively/additionally, a microscope may be part of or connected to a system as described in connection with one or more of the figures. FIG. 1 shows a schematic illustration of a surgical system such as a surgical microscope 100 configured to perform a method described herein. The system can include an imaging device 104 and an apparatus 102 which can include a computer system. The system is configured to take images and is connected to the computer system. The computer system can be configured to execute at least a part of a method described herein. The computer system may be configured to execute a machine learning algorithm. The computer system and microscope may be separate entities but can also be integrated together in one common housing. The computer system may be part of a central processing system of the microscope and/or the computer system may be part of a subcomponent of the microscope, such as a sensor, an actor, a camera or an illumination unit, etc. of the microscope.

The computer system may be a local computer device (e.g. personal computer, laptop, tablet computer or mobile phone) with one or more processors and one or more storage devices or may be a distributed computer system (e.g. a cloud computing system with one or more processors and one or more storage devices distributed at various locations, for example, at a local client and/or one or more remote server farms and/or data centers). The computer system may comprise any circuit or combination of circuits. In one embodiment, the computer system may include one or more processors which can be of any type. As used herein, processor may mean any type of computational circuit, such as but not limited to a microprocessor, a microcontroller, a complex instruction set computing (CISC) microprocessor, a reduced instruction set computing (RISC) microprocessor, a very long instruction word (VLIW) microprocessor, a graphics processor, a digital signal processor (DSP), multiple core processor, a field programmable gate array (FPGA), for example, of a microscope or a microscope component (e.g. camera) or any other type of processor or processing circuit. Other types of circuits that may be included in the computer system may be a custom circuit, an application-specific integrated circuit (ASIC), or the like, such as, for example, one or more circuits (such as a communication circuit) for use in wireless devices like mobile telephones, tablet computers, laptop computers, two-way radios, and similar electronic systems. The computer system may include one or more storage devices, which may include one or more memory elements suitable to the particular application, such as a main memory in the form of random access memory (RAM), one or more hard drives, and/or one or more drives that handle removable media such as compact disks (CD), flash memory cards, digital video disk (DVD), and the like. The computer system may also include a display device, one or more speakers, and a keyboard and/or controller, which can include a mouse, trackball, touch screen, voice-recognition device, or any other device that permits a system user to input information into and receive information from the computer system.

Some or all of the method steps may be executed by (or using) a hardware apparatus, like for example, a processor, a microprocessor, a programmable computer or an electronic circuit. In some embodiments, some one or more of the most important method steps may be executed by such an apparatus.

Depending on certain implementation requirements, embodiments of the invention can be implemented in hardware or in software. The implementation can be performed using a non-transitory storage medium such as a digital storage medium, for example a HDD (hard disk drive), an SSD (solid state drive), a floppy disc, a DVD, a Blu-Ray, a CD, a ROM, a PROM, and EPROM, an EEPROM or a FLASH memory, having electronically readable control signals stored thereon, which cooperate (or are capable of cooperating) with a programmable computer system such that the respective method is performed. Therefore, the digital storage medium may be computer readable.

Some embodiments according to the invention comprise a data carrier having electronically readable control signals, which are capable of cooperating with a programmable computer system, such that one of the methods described herein is performed.

Generally, embodiments of the present invention can be implemented as a computer program product with a program code, the program code being operative for performing one of the methods when the computer program product runs on a computer. The program code may, for example, be stored on a machine readable carrier.

Other embodiments comprise the computer program for performing one of the methods described herein, stored on a machine readable carrier.

In other words, an embodiment of the present invention is, therefore, a computer program having a program code for performing one of the methods described herein, when the computer program runs on a computer.

A further embodiment of the present invention is, therefore, a storage medium (or a data carrier, or a computer-readable medium) comprising, stored thereon, the computer program for performing one of the methods described herein when it is performed by a processor. The data carrier, the digital storage medium or the recorded medium are typically tangible and/or non-transitionary. A further embodiment of the present invention is an apparatus as described herein comprising a processor and the storage medium.

A further embodiment of the invention is, therefore, a data stream or a sequence of signals representing the computer program for performing one of the methods described herein. The data stream or the sequence of signals may, for example, be configured to be transferred via a data communication connection, for example, via the internet.

A further embodiment comprises a processing means, for example, a computer or a programmable logic device, configured to, or adapted to, perform one of the methods described herein.

A further embodiment comprises a computer having installed thereon the computer program for performing one of the methods described herein.

A further embodiment according to the invention comprises an apparatus or a system configured to transfer (for example, electronically or optically) a computer program for performing one of the methods described herein to a receiver. The receiver may, for example, be a computer, a mobile device, a memory device or the like. The apparatus or system may, for example, comprise a file server for transferring the computer program to the receiver.

In some embodiments, a programmable logic device (for example, a field programmable gate array) may be used to perform some or all of the functionalities of the methods described herein. In some embodiments, a field programmable gate array may cooperate with a microprocessor in order to perform one of the methods described herein. Generally, the methods are preferably performed by any hardware apparatus.

LIST OF REFERENCE SIGNS

| | |
|---|---|
| apparatus | 102 |
| processor(s) | 101 |
| image | 105 |
| display | 111 |
| memory | 107 |
| surgical microscope | 100 |
| output interface | 110 |
| imaging device | 104 |
| medical instrument | 210 |
| depth direction | y |
| horizontal direction | x |
| OCT image | 300 |
| first feature | 310 |
| second feature | 320 |
| third feature | 330 |
| fourth feature | 340 |
| eye | 350 |
| superimposed image | 400 |
| | 405 |
| outer edge | 410 |
| inner edge | 420 |
| first reference | 451 |
| second reference | 452 |
| unsmooth region | 460 |
| stable region | 470 |
| eye | 500 |
| epithelium 510 | 510 |
| Bowman layer | 520 |
| stroma | 530 |
| Descemet membrane | 540 |
| endothelium | 550 |
| first region | 561 |
| second region | 562 |
| third region | 563 |
| fourth region | 564 |
| superimposed image | 600 |
| cross-sectional image | 605 |
| outer edge | 610 |
| inner edge | 620 |
| first reference | 651 |
| line | 651a |
| dots | 651b |
| second reference | 652 |
| third reference | 653 |
| first image | 701 |
| subsequent image | 702 |
| edge | 710 |
| first reference | 751 |
| second reference | 752 |
| method | 800 |
| determine an edge | 810 |
| determine a superimposed image | 820 |
| outputting | 830 |
| displaying | 840 |
| cross-sectional image | 901 |
| first edge | 910 |
| second edge | 920 |
| first reference | 951 |
| second reference | 952 |
| third reference | 953 |
| superimposed mage | 1000 |
| cross-sectional image | 1005 |
| edge | 1010 |
| second edge | 1020 |
| first reference | 1051 |
| second reference | 1052 |

The invention claimed is:

1. An apparatus for processing image data, comprising:

one or more processors configured to:

generate a cross-sectional image and a subsequent cross-sectional image of a live tissue;

determine a feature in the cross-sectional image of the live tissue;

determine a superimposed image by superimposing a first reference and a second reference on the cross-sectional image or the subsequent cross-sectional image of the live tissue, the first reference being determined based on the determined feature and the second reference being determined based on an offset from the first reference;

identify a stable region and an unstable region of the determined feature, the unstable region corresponding to an area of surgical activity; and update the first reference in the subsequent cross-sectional image by tracking a position of the stable region, while disregarding changes in the unstable region; and an output interface configured to output image data of the superimposed image for displaying the superimposed image.

2. The apparatus of claim 1, wherein the offset is in a depth direction.

3. The apparatus of claim 2, wherein the second reference is offset from the first reference by 20-500 μm.

4. The apparatus of claim 1, wherein the first reference includes a first plurality of points along a line.

5. The apparatus of claim 4, wherein the apparatus is configured to accept user input for adjusting at least one of the first reference or the second reference, including at least one of:

offsetting the first plurality of points, offsetting a second plurality of points of the second reference, adjusting a first curvature of the first plurality of points, adjusting a second curvature of the second plurality of points, adjusting a first path of the first plurality of points, or adjusting a second path of the second plurality of points.

6. The apparatus of claim 1, wherein the apparatus is further configured to:

receive real time data, and determine the subsequent cross-sectional image based on the real time data.

7. The apparatus of claim 1, wherein the apparatus is further configured to:

move at least one of the first reference or the second reference, based on user input.

8. The apparatus of claim 1, wherein the apparatus is configured to determine the feature based on at least one of: image recognition, machine learning, threshold determination, or edge detection.

9. The apparatus of claim 1, wherein the apparatus is configured to:

receive real time data from at least one of optical coherence or ultrasound, and update at least one of the cross-sectional image or the subsequent cross-sectional image in real time.

10. The apparatus of claim 1, further comprising:

a display for displaying the superimposed image, the display including a user interface.

11. The apparatus of claim 10, wherein at least one of the first reference and the second reference includes:

a curved line segment, and at least one highlighted point on the curved line segment;

wherein the at least one highlighted point is configured to receive user input for adjusting at least one of the respective first and second references.

12. A non-destructive imaging device, comprising:

the apparatus of claim 1, wherein the non-destructive imaging device is configured to determine the cross-sectional image and the subsequent cross-sectional image of the live tissue.

13. A surgical microscope, comprising:

the non-destructive imaging device of claim 12, wherein the non-destructive imaging device includes an optical coherence imaging device configured to determine the cross-sectional image of the live tissue.

14. A method of image guidance, comprising:

determining a feature in a cross-sectional image of a live tissue;

determining a superimposed image by superimposing a first reference and a second reference on the cross-sectional image or a subsequent cross-sectional image of the live tissue, the first reference being determined based on the determined feature and the second reference being determined based on an offset from the first reference;

identifying a stable region and an unstable region of the determined feature, the unstable region corresponding to an area of surgical activity;

updating the first reference in the subsequent cross-sectional image by tracking a position of the stable region, while disregarding changes in the unstable region; and outputting image data of the superimposed image for displaying the superimposed image.

* * * * *